(12) United States Patent
Zengerle et al.

(10) Patent No.: US 6,399,395 B1
(45) Date of Patent: Jun. 4, 2002

(54) DEVICE AND METHOD OF APPLYING MICRODROPLETS TO A SUBSTRATE

(75) Inventors: Roland Zengerle, Villingen-Schwenningen; Nicolaus Hey, Eschbronn-Mariazell; Holger Gruhler, Tuningen; Michael Freygang, Villingen-Schwenningen; Martin Müller, Dietingen, all of (DE)

(73) Assignee: Hahn-Schickard-Gesellschaft für angewandte Forschung e.V. (DE)

( * ) Notice: Subject to any disclaimer, the term of this patent is extended or adjusted under 35 U.S.C. 154(b) by 0 days.

(21) Appl. No.: 09/416,129

(22) Filed: Oct. 12, 1999

(30) Foreign Application Priority Data

Mar. 23, 1999 (DE) .......................................... 199 13 076

(51) Int. Cl.⁷ ................................................ C12M 1/36
(52) U.S. Cl. ................. 436/180; 435/286.4; 435/287.3; 436/518; 427/2.13; 422/100
(58) Field of Search .................... 435/6, 810, 286.4, 435/287.3; 436/501, 518, 524, 527, 180; 239/1, 3, 34; 427/2.1, 2.13, 421, 445; 422/100

(56) References Cited

U.S. PATENT DOCUMENTS

| | | |
|---|---|---|
| 5,508,200 A | 4/1996 | Tiffany et al. |
| 5,551,487 A | 9/1996 | Gordon et al. |
| 5,658,802 A * | 8/1997 | Hayes et al. ................. 436/518 |
| 5,763,170 A * | 6/1998 | Raybuck ......................... 435/6 |
| 5,847,105 A | 12/1998 | Baldeschwieler et al. |
| 6,001,309 A * | 12/1999 | Gamble et al. ............. 436/518 |
| 6,232,072 B1 * | 5/2001 | Fisher ............................. 435/6 |
| 6,323,072 B1 * | 11/2001 | Caren et al. ................. 436/518 |

FOREIGN PATENT DOCUMENTS

| | | |
|---|---|---|
| DE | 30 04 555 A1 | 8/1981 |
| DE | 31 23 796 A1 | 3/1982 |
| DE | 198 02 368 C1 | 8/1999 |
| JP | 07116575 A | 5/1995 |
| WO | WO 93/09668 | 5/1993 |
| WO | WO 93/10910 | 6/1993 |
| WO | WO 97/01393 | 1/1997 |
| WO | WO 97/45730 | 12/1997 |
| WO | WO 98/51999 | 11/1998 |

\* cited by examiner

Primary Examiner—Joseph W. Drodge
(74) Attorney, Agent, or Firm—Patton Boggs LLP (57) ABSTRACT

A device for applying microdroplets to a substrate includes a dosing head having a nozzle orifice and a liquid storage area in fluid communication with the orifice. A drive applies an acceleration to the dosing head. A quantity of liquid in the storage area cannot follow the acceleration due to its inertia. This inertia causes microdroplets to be driven out of the nozzle onto the substrate. In one embodiment, the dosing head includes a plurality of nozzle orifices each having an associated liquid storage area, so that a plurality of different analytes are deposited on the substrate.

16 Claims, 6 Drawing Sheets

DEVICE AND METHOD OF APPLYING MICRODROPLETS TO A SUBSTRATE

BACKGROUND OF THE INVENTION

1. Field of the Invention

The present invention relates to a device for applying at least one microdroplet to a substrate and it relates to a dosing head which is adapted to be used in such a device. The present invention relates additionally to a method of applying at least one microdroplet to a substrate. In particular, the present invention relates to devices and methods which are suitable for producing so-called biochips in the case of which a plurality of different analytes are applied to a substrate so as to detect different substances in an unknown sample.

2. Description of Prior Art

The increasing degree to which the genomes of human beings, animals and plants are deciphered creates a large number of new possibilities from the diagnosis of genetically based illnesses to the much faster search for pharmaceutically interesting agents. For example, the above-mentioned biochips will be used in the future for examining food with regard to a large number of possible, genetically modified constituents. In another field of use, such biochips can be used for detecting the precise genetic defect in the case of genetically based illnesses so as to derive therefrom the ideal strategy for treating the illness.

The biochips which are adapted to be used for these applications normally consist of a carrier material, i.e. a substrate, having applied thereto a large number of different substances in the form of a raster. Typical raster distances in the array range from 100 $\mu$m to 1,000 $\mu$m. The variety of different substances, which are referred to as so-called analytes, on a biochip ranges from a few different substances to a few 100,000 different substances per substrate, depending on the respective case of use. Each of these different analytes can be used for reaffirming the presence of a specific substance in an unknown sample.

When an unknown sample liquid is applied to a biochip, reactions occur in the case of specific analytes; these reactions can be detected through suitable methods, e.g. fluorescence detection. The number of different analytes on the biochip corresponds to the number of different constituents in the unknown sample liquid which can be analyzed simultaneously by means of the respective biochip. Such a biochip is therefore a diagnostic tool with the aid of which an unknown sample can be examined with regard to a large number of constituents simultaneously and purposefully.

For applying the analytes to a substrate for the production of such a biochip, three fundamentally different methods are known at present. These methods are used alternatively, depending on the number of biochips required and depending on the necessary number of analytes per chip.

The first method is referred to as "contact printing"; this method uses a bundle of steel capillaries filled with different analytes in the interior thereof. This bundle of steel capillaries is stamped onto the substrate. When the bundle is being removed, the analytes adhere to the substrate in the form of microdroplets. In the case of this method, the quality of the printing pattern is, however, influenced very strongly by the effect of capillary forces and, consequently, it depends on a large number of critical parameters, e.g. the quality of and the coating on the surface of the substrate, the precise geometry of the nozzle and, primarily, the media used. In addition, the method is very susceptible to contaminations of the substrate and of the nozzles. The number of analytes which can be dealt with by the above-described method is up to a few hundred per substrate.

In a second method of producing biochips, which is normally referred to as "spotting", so-called microdispensers are used in most cases, which, similar to ink-jet printers, are capable of firing individual microdroplets of a liquid onto a substrate in response to a suitable control command. Such a method is called "drop-on-demand". Such microdispensers are commercially available from some firms. The advantage of this method is to be seen in the fact that it permits a contact-free application of the analytes to a substrate, the influence of capillary forces being then of no importance. An essential problem is, however, that it is very expensive and extremely difficult to arrange a large number of nozzles, which have each supplied thereto a different medium, in parallel and in an array, respectively. The limiting element is in this case the actorics and the media logistics, which cannot be miniaturized to the desired extent.

The so-called "synthesis method" is nowadays used as a third method of producing biochips; in this method, the analytes, which normally consist of a chain of linked nucleic acids, are produced chemically on the substrate, i.e. they are synthesized. For delimiting the spatial position of the different analytes, methods are used which are known e.g. from the field of microelectronics, e.g. lithographic methods with masking techniques. Among the methods mentioned hereinbefore, this synthesis method is by far the most expensive one, but it permits the production of the greatest variety of analytes on a chip, the order of magnitude of this variety being 100,000 different analytes per substrate.

SUMMARY OF THE INVENTION

It is the object of the present invention to provide methods and devices by means of which microdroplets can be applied individually or in the form of a regular pattern to a substrate inexpensively and accurately.

In accordance with a first aspect of the present invention, this object is achieved by a device for applying at least one microdroplet to a substrate, comprising:

a dosing head with at least one nozzle orifice; and a drive means for applying to the dosing head an acceleration of such a nature that a microdroplet is driven out of the nozzle orifice and onto the substrate due to inertia.

In accordance with a second aspect of the present invention, this object is achieved by a dosing head comprising a dosing head body in which the at least one nozzle orifice is formed, said dosing head body including in addition a liquid storage area which is in fluid communication with the nozzle orifice in such a way that, due to the inertia of a liquid present in said liquid storage area, a microdroplet can be driven out of said nozzle orifice by applying to the dosing head an acceleration.

The liquid storage area of the inventive dosing head can preferably be formed by a standpipe extending away from the nozzle orifice in a direction opposite to the direction in which the microdroplet can be driven out of the dosing head.

In accordance with a third aspect of the present invention, this object is achieved by a method of applying at least one microdroplet to a substrate, said method comprising the following steps:

a) filling a liquid storage area, which is in fluid communication with a nozzle orifice, with an amount of liquid, said nozzle orifice and said liquid storage area being formed in a dosing head; and b) applying to said dosing head an acceleration of such a nature that a microdroplet is driven out of the nozzle orifice due to the inertia of the amount of liquid.

Hence, the present invention provides devices and methods by means of which biochips can be produced at a reasonable price and in high numbers of pieces. The present invention is based on the finding that microdroplets can be driven out of the dosing head by means of a mechanical acceleration which is applied to a dosing head by an external mechanical system. Suitable devices of an arbitrary nature can be used for the external mechanical system, which represents a drive means, these suitable devices being e.g. piezo-bending transducers, piezo-stacks, pneumatic drives and the like. A liquid contained in areas which are in fluid communication with the nozzle orifice is then acted upon by inertia forces, these areas being e.g. the nozzle itself, a media line and a reservoir. Since the liquid is not rigidly connected to the dosing head, these inertia forces have the effect that the liquid is accelerated relative to the dosing head carrying the liquid. Hence, the liquid starts to move relative to the dosing head. When this relative movement between the liquid contained in the nozzle and the nozzle orifice is sufficiently large, a microdroplet will tear off at the nozzle. The size of this drop is determined by the magnitude and the duration of the accleration of the dosing head, the size of the liquid mass whose inertia causes the ejection, the diameter of the nozzle and the flow resistance of the movement of the liquid in the dosing head. The direction of the acceleration applied to the dosing head must be oriented such that the liquid is flung out of the nozzle due to its inertia but does not withdraw into liquid storage areas or media lines in the dosing head.

By means of the present invention, a plurality of microdroplets is preferably applied to a substrate simultaneously so that e.g. a biochip for which different biologically relevant substances are applied to a substrate in a regular pattern can be produced inexpensively and reliably. Due to the acceleration of the dosing head, it is possible to drive a microdroplet out of each individual nozzle in a dosing head at the same time, the inertia of the liquid being utilized for this purpose.

The dosing head can have applied thereto different accelerations so as to cause an ejection of liquid droplets. One possibility is to accelerate the dosing head from a position of rest adjacent the substrate very strongly so as to cause the dosing head to move away from the substrate. An alternative possibility is to decelerate the dosing head abruptly while it is carrying out a continuous movement towards the substrate; this deceleration can be supported e.g. by a mechanical stop. In addition, it is also possible to provide a mechanically sufficiently stiff holder for the dosing head, which is excited in ranges of the natural frequency thereof in such a way that the holder and, consequently, the dosing head carry out half an oscillation. In this case, the maximum accleration occurs at the point of reversal of the oscillation so that the holder and the dosing head are arranged such that the dosing head is disposed adjacent the substrate at the point of reversal of the oscillation.

The dosing head according to the present invention may comprise one or a plurality of nozzles, the nozzles being arranged at a distance from one another which corresponds to the distance at which the fluid droplets to be applied to the substrate are to be spaced from one another on this substrate. When the nozzles are to be arranged in very closely spaced relationship with one another, i.e. when a very narrow array of different substances is to be produced on the substrate, it will be advantageous when each nozzle is connected to a larger external reservoir via a media line of its own; through these external reservoirs, each nozzle can be supplied with a specific liquid. When the distances between the individual nozzles are large enough for permitting the nozzles to be supplied with liquid by conventional methods, e.g. by standard automatic pipetting devices, the media lines and the external liquid reservoirs can be dispensed with. In this case, the liquid reservoir can be arranged directly above the nozzle.

Such a dosing head can now be decelerated abruptly directly in front of the substrate while carrying out a movement towards the substrate. Due to its inertia and in view of the fact that it is not rigidly connected to the dosing head, the liquid continues this movement and is flung out of the nozzle and onto the substrate. Alternatively, a static dosing head, which is located directly above a substrate, can be accelerated abruptly in a direction away from the substrate. Due to its inertia and in view of the fact that it is not rigidly connected to the dosing head, the liquid cannot follow this movement. It leaves the nozzle in a direction opposite to the direction of movement of the dosing head and is first suspended freely in space before the drops fall onto the substrate due to the force of gravity, the movement of the dosing head being caused by the acceleration away from the substrate. A device can be provided for producing an electrostatic field between the dosing head and the substrate so as to support the application of the droplets to the substrate in this way.

In each of the two above-mentioned cases, it will be advantageous when the acceleration of the dosing head is effected at a position at which the distance between the nozzles in the dosing head and the substrate is very small. This guarantees that, if satellite drops form during the separation of the microdroplets, these satellite drops will merge with the mother drop on the substrate at the latest. Due to the small distance, it is guaranteed that the satellite drops will land on the mother drop even if they left the nozzle at a slightly different angle.

It follows that the present invention provides devices and methods by means of which microdroplets, especially microdroplets of biologically relevant substances, can be produced and applied to a substrate in a regular pattern.

BRIEF DESCRIPTION OF THE DRAWINGS

In the following, preferred embodiments of the present invention will be explained in detail making reference to the drawings enclosed, in which:

FIGS. 5, 6, 7a) and 7b) show schematic cross-sectional views of alternative embodiments of dosing heads according to the present invention.

DESCRIPTION OF PREFERRED EMBODIMENTS OF THE INVENTION

Figure 1:
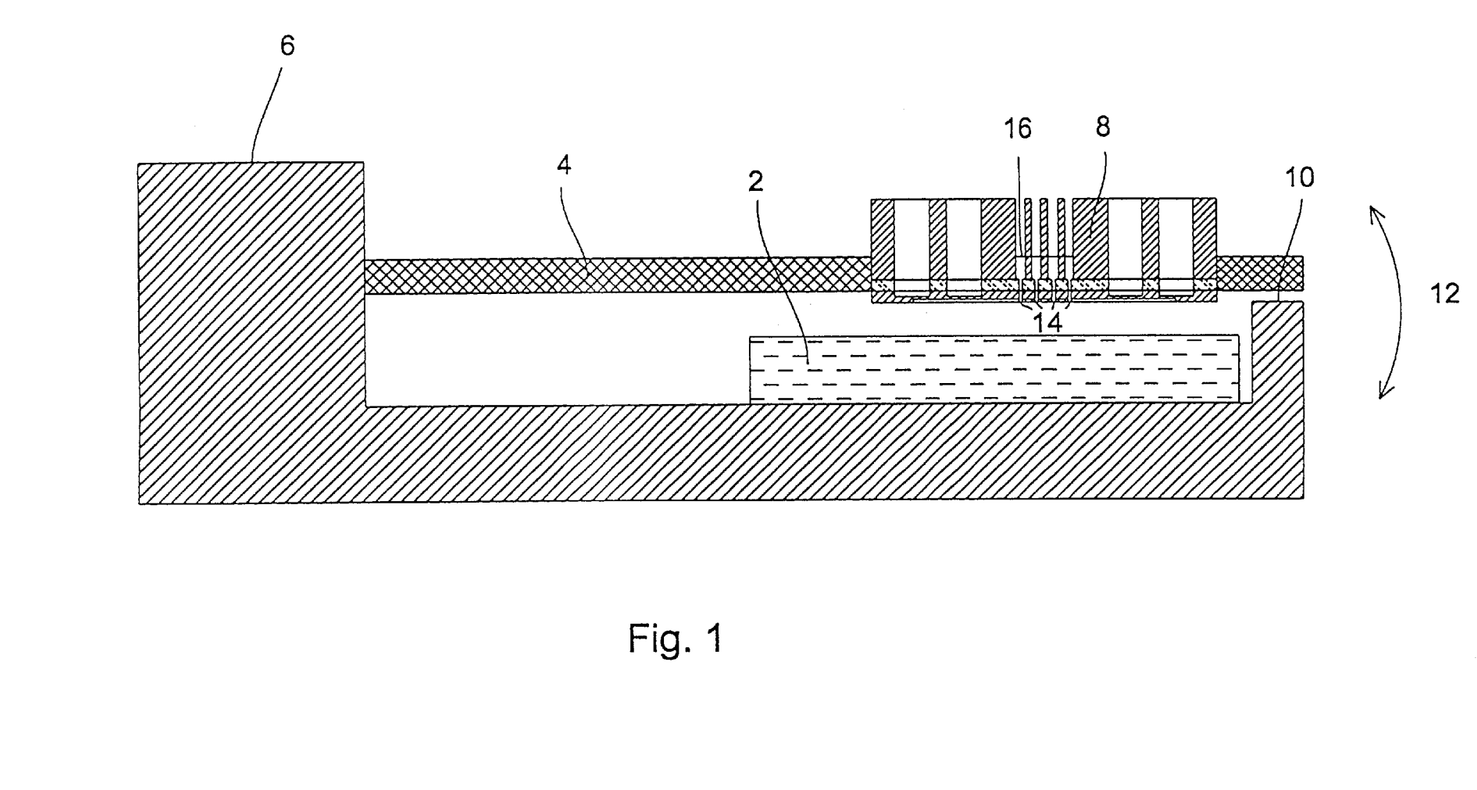
FIG. 1 shows schematically a preferred embodiment of a device according to the present invention used for applying microdroplets to a substrate.

FIG. 1 shows a schematic cross-sectional view of a preferred embodiment of a device according to the present invention used for applying microdroplets to a substrate 2. As can be seen in FIG. 1, a piezo-bending transducer 4 is fixed at one end thereof in a holder 6, a dosing head 8 being attached to the non-fixed end of the piezo-bending transducer 4. Preferred embodiments of the dosing head 8 will be explained in detail hereinbelow making reference to FIGS. 2 to 7b. As can additionally be seen in FIG. 1, the holder 6 is implemented such that it defines a stop 10 by means of which a movement of the piezo-bending transducer 4 and, consequently, of the dosing head 8 is limited downwards in the representation according to FIG. 1, this movement being shown schematically by arrow 12. The dosing head 8 is provided with a plurality of nozzle orifices 14 above which a respective amount of liquid is arranged, as has been indicated schematically by reference numeral 16 and as will be explained in more detail in the following.

When the device is in operation, the piezo-bending transducer 4 is driven for moving the dosing head 8 downwards. This movement is finished abruptly, when the right end of the piezo-bending transducer strikes against the stop 10 so that the dosing head 8 is subjected to a strong decleration. Due to this strong deceleration, the inertia of the amount s of liquid 16 arranged above the nozzle orifices 14 causes a microdroplet to be expelled from the nozzle orifices 14 and to impinge upon the substrate 2. If these amounts of liquid consist of different liquids, an array of analytes can be produced on the substrate 2 by means of the plurality of nozzle orifices 14. As has been shown schematically in FIG. 1, it will be advantageous when the dosing head 8 is arranged directly adjacent the substrate at the moment at which it is subjected to the deceleration so as to permit exact positioning of the microdroplets on the substrate 2 and so that possible satellite components of the droplet will be caused to merge with the mother droplet.

The actual profile of the acceleration to which the dosing head is subjected can be varied via the edge steepness of the voltage signal by means of which the bending transducer is driven. The amplitude of the movement can be adapted simply by the length of the piezo-bending transducer or the amplitude of the voltage signal; as can be seen in FIG. 1, a stop 10 can be provided for supporting the abrupt deceleration of the dosing head. Alternatively, it may also suffice to cause a sudden deceleration of the dosing head via an electric control signal having a high edge steepness.

In addition to the piezo-bending transducer shown in FIG. 1, a piezo-stack actor can be used as a drive means for abruptly accelerating the dosing head. In this case, it will, however, be advisable to enlarge the length of distance travelled by the actor, which is typically between 20 $\mu$m and 100 $\mu$m, by a mechanical lever. On the whole, it will be advantageous when the whole distance travelled by the dosing head is larger than the diameter of the drop which is to be ejected from the nozzle. Otherwise, the danger exists that, in the case of very small movements, a drop which has already left the nozzle will be drawn back into the nozzle before it can tear off completely. In addition, it may be adavantageous to move the dosing head after the abrupt deceleration, after the movement of the dosing head towards the substrate, at high speed in a direction away from the substrate so as to influence the tearing of the drop in an advantageous manner.

Figure 2:
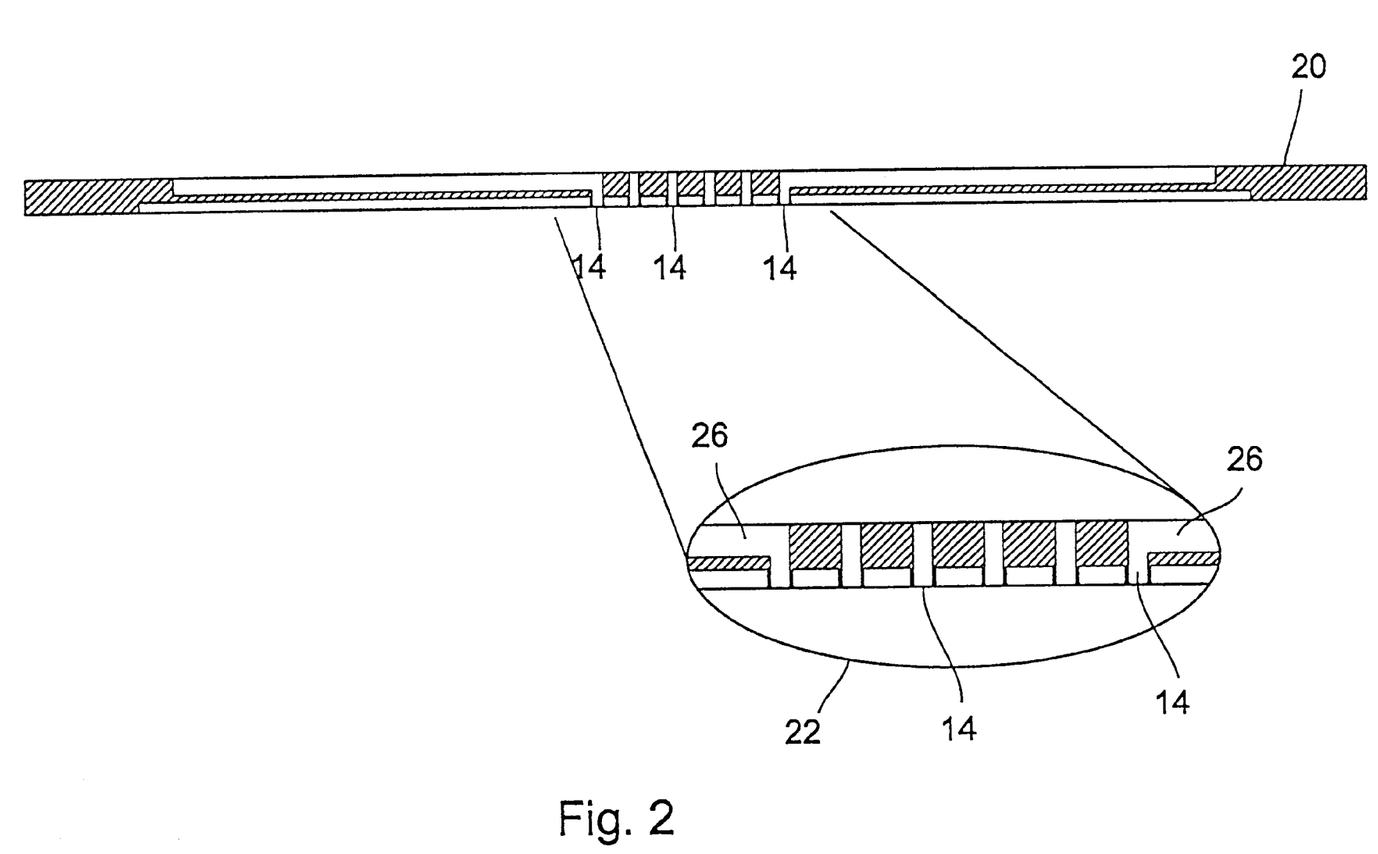
FIG. 2 shows schematically a cross-sectional view of an embodiment of a dosing head according to the present invention.

On the whole, it will be of advantage when the dosing head 8 and the mechanical driving device, which consists of the piezo-bending transducer 4 and the holder 6 in the embodiment according to FIG. 2, are implemented modularly so that the dosing head can be replaced easily.

Making reference to FIGS. 2 to 7b, embodiments of the dosing head according to the present invention will be explained in more detail in the following. The dosing head may, for example, be a chip produced by silicon micromechanical methods. A schematic cross-sectional view of such a chip is shown in FIG. 2 and designated by reference numeral 20; FIG. 2 additionally comprises an enlarged view 22 of the area in which the nozzle orifices 14 are arranged. The nozzles 14 are microstructured in the lower surface of the chip 20 and exposed relative to the surrounding silicon surface. In FIG. 2, six juxtaposed nozzles 14 are shown, a bottom view of the chip with the nozzles 14 structured in the lower surface thereof being shown in FIG. 3; in FIG. 3, it can be seen that the embodiment of a dosing head shown in this figure comprises twenty-four nozzles. In this FIG. 3, it can also be seen that the nozzles are exposed relative to the surrounding silicon surface, the dosing head being surrounded by a border 24 which can be seen in the bottom view of this dosing head. The nozzles 14 of the embodiment shown in this figure are connected to media reservoirs, which can e.g. also be integrated on the chip, via media lines 26; in FIG. 2 only two media lines for the outermost nozzles are shown.

Figure 4:
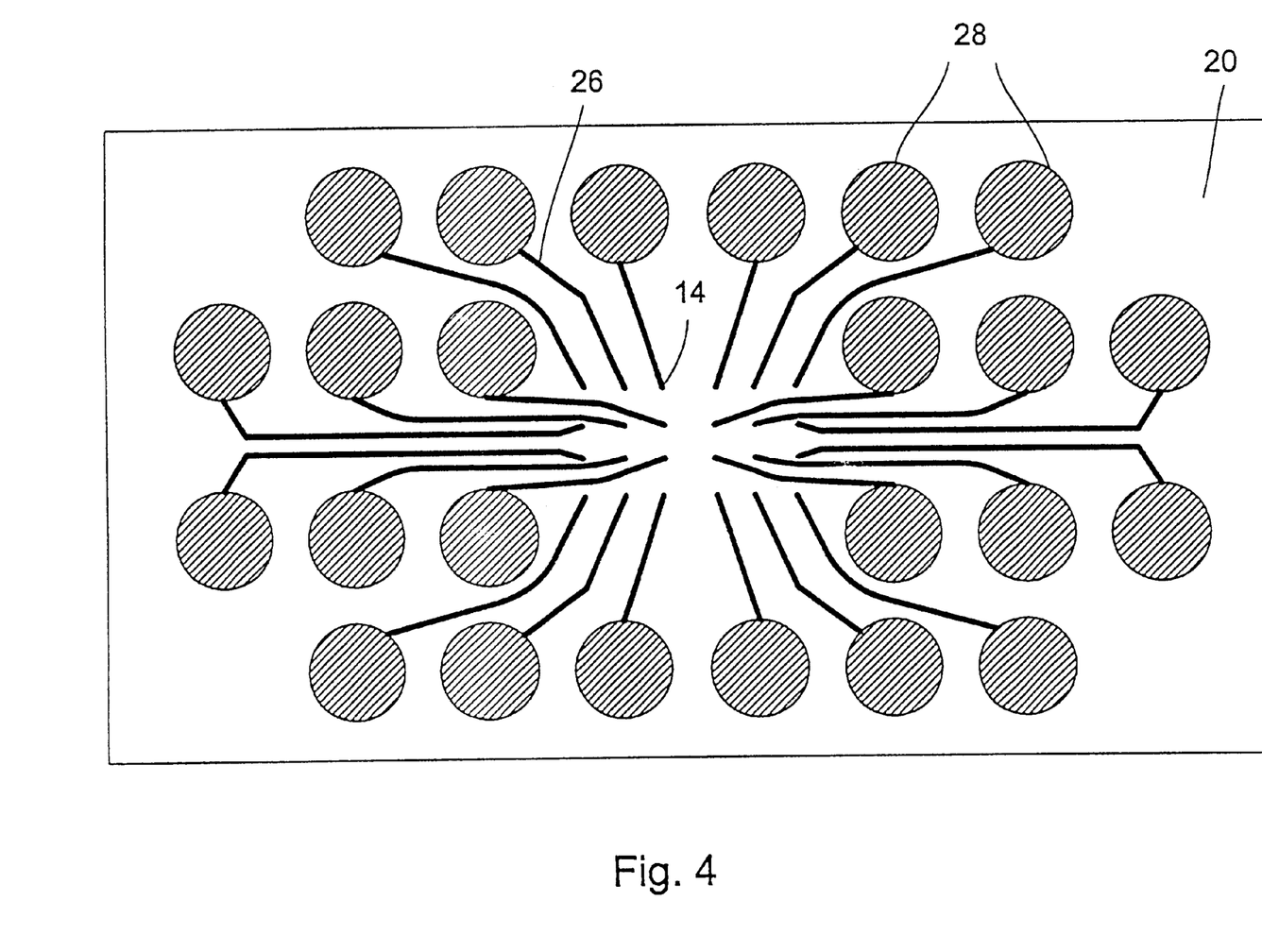
FIG. 4 shows schematically a top view of the dosing head shown in FIG. 2.

A schematic top view of the dosing head 20 represented in FIG. 2 is shown in FIG. 4; this FIG. 4 shows twenty-four media reservoirs 28 which are connected to respective nozzles 14 via media lines 26. In the embodiment shown, the media reservoirs 28 are structured in the chip surface which is opposed to the nozzles 14, the chip forming the dosing head. The media reservoirs 28 are preferably implemented such that they can be filled automatically with liquids by standard automatic pipetting devices. For this purpose, they may e.g. have identical diameters and distances, like the chambers of a known 348-well microtiter plate. The liquid from the media reservoirs 28 is preferably drawn into the nozzles 14 via the media lines 26 by means of capillary forces. The media lines 26 serve to supply the closely spaced nozzles 14 with liquid from a larger reservoir 28.

Figure 3:
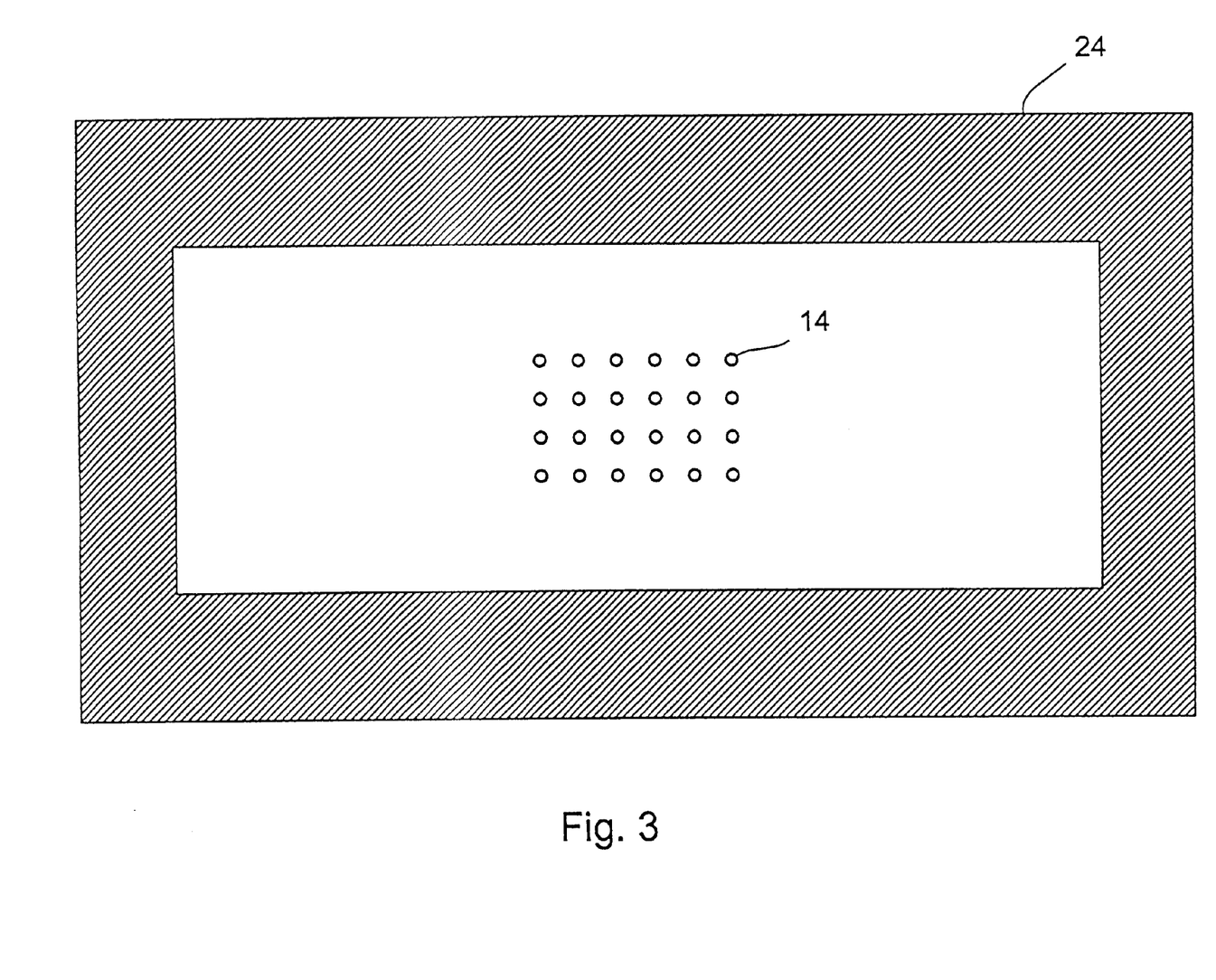
FIG. 3 shows schematically a bottom view of the dosing head shown in FIG. 2.

The nozzles described with reference to FIGS. 2 to 4 may have a diameter of e.g. 200 $\mu$m and also the media lines 26 may have a width of 200 $\mu$m. Hence, twenty-four nozzles can easily be arranged in an array of six times four nozzles, as can be seen in FIG. 3, the distance between the individual nozzles being 1 mm. The limiting factor for the number of nozzles that can be arranged in an array is the width of the connection passages interconnecting the nozzles and the reservoirs. These connection passages must be conducted outwards between the nozzles. When the width of these passages is reduced, it is also possible to accommodate 48, 96 or more nozzles on one dosing head.

Figure 5:
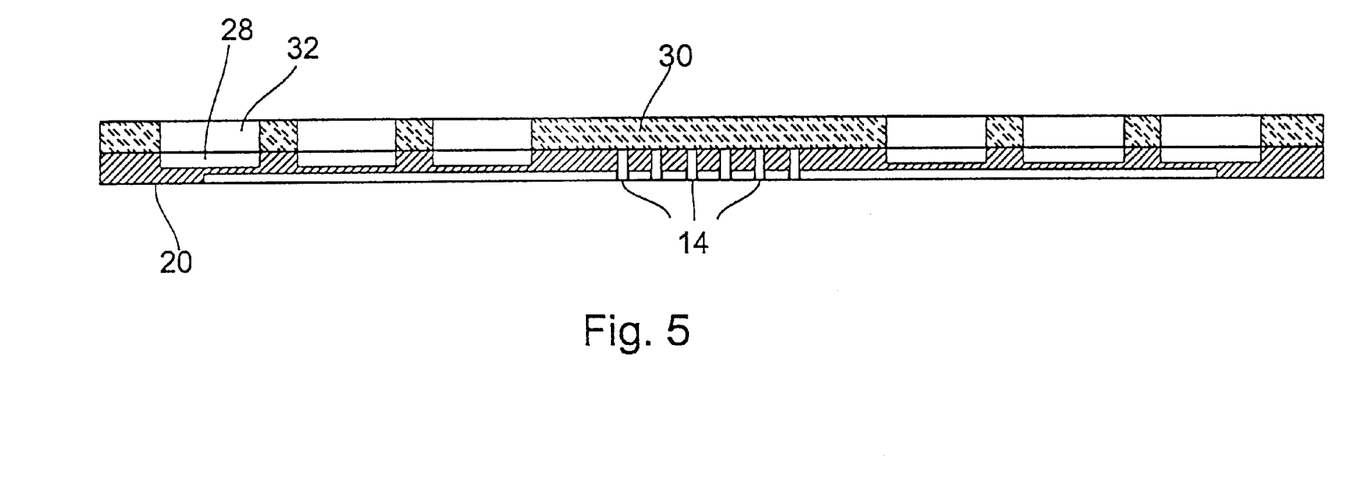

In order to prevent the liquids from different media lines from mixing in the area of the nozzles, the upper surface of the chip can be covered either with a hydrophobic layer (not shown) or with a foil or with a further silicon chip or glass chip bonded to the upper surface of the chip. Such a cover chip 30 is shown in FIG. 5; in this figure, it can be seen that the cover chip 30 is provided with openings 32 permitting the media reservoir 28 to be filled. The cover layer 30 used may preferably be an elastic foil, which, due to its yieldingness, may have advantages in comparison with a rigid cover plate.

In the embodiments of a dosing head described with reference to FIGS. 2 to 5, the dosing quality can depend on the flow resistances of the liquid in the media lines. In accordance with a preferred embodiment, the amount of liquid placed directly above the nozzle of the dosing head according to the present invention may therefore be increased so as to achieve that the dosing quality is rendered independent of the flow resistances of the media lines.

Figure 6:
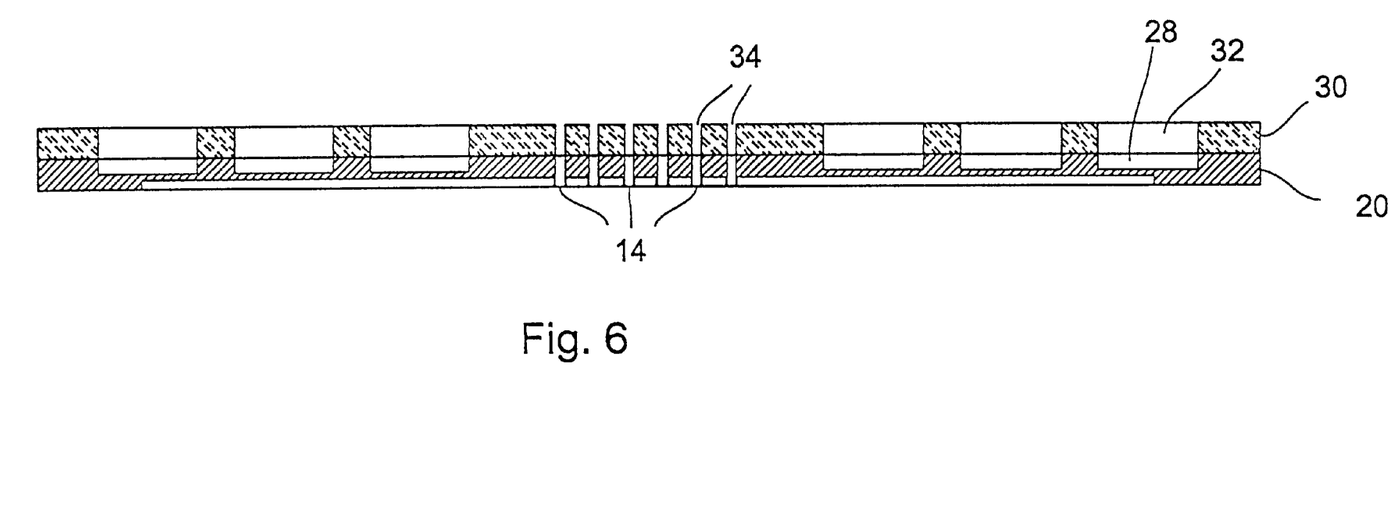
Figure 7:
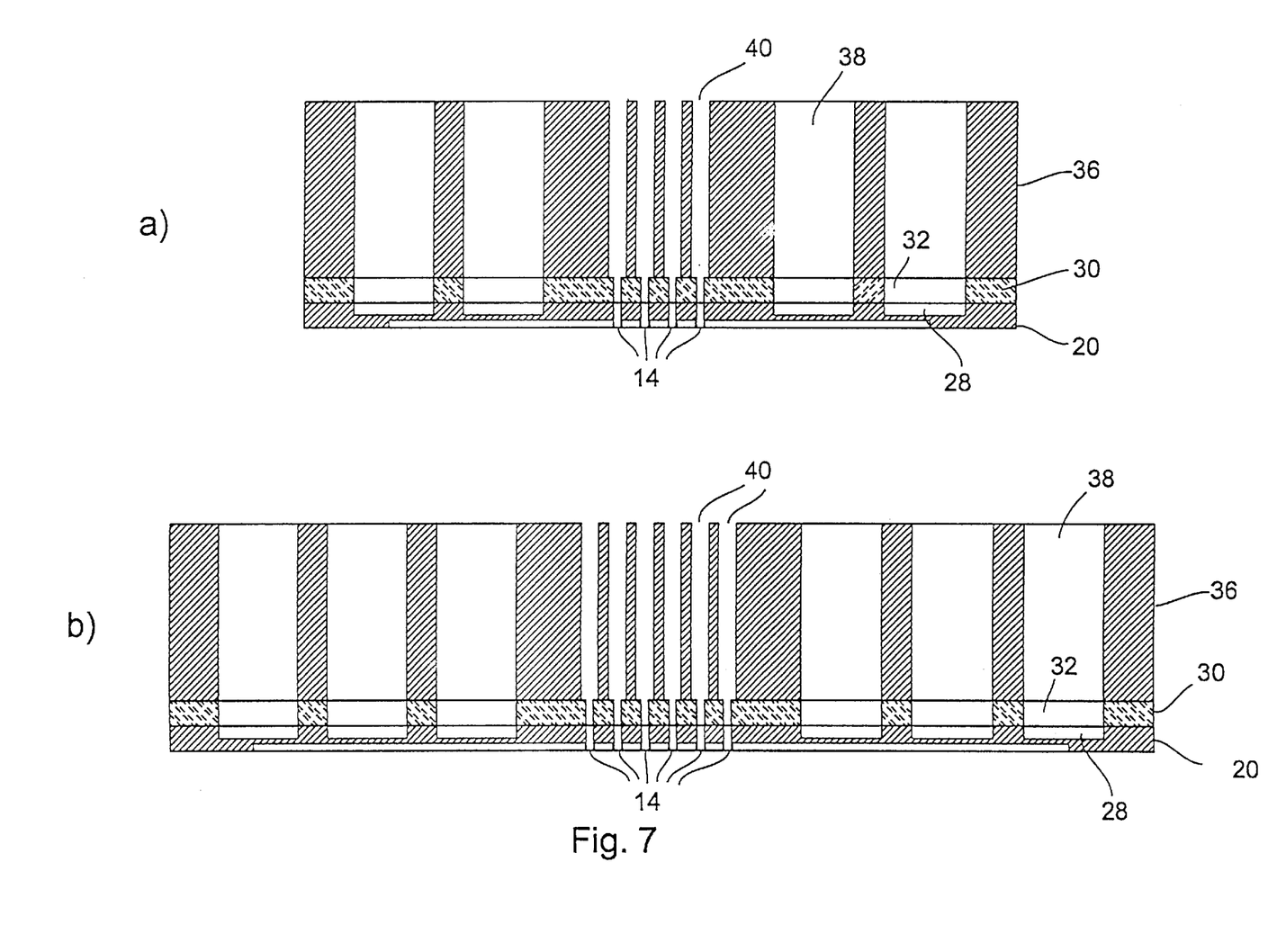

Embodiments of dosing heads in the case of which such an increase of the amount of liquid above the nozzles has been realized are shown in FIGS. 6, 7a and 7b. As can be seen in FIG. 6, a respective axial standpipe 34, which extends in a direction opposite to the ejection direction, is arranged above each of the nozzles 14. These standpipes 34 can be connected to the media lines via a T-shaped connection (not shown) close to the nozzle, these media lines being located on the upper surface of the chip as before. The standpipes 34 fill with liquid from the media lines due to capillary forces alone. It should be pointed out that, for reasons of clarity, the media lines are not shown in the cross-sectional views of FIGS. 5 to 7b.

FIGS. 7a) and 7b) show two sectional views of the dosing head 8 used in the device shown in FIG. 1, the sectional view in FIG. 7a) showing four nozzles 14 along the transverse direction, whereas the sectional view in FIG. 7b) shows six nozzles 14 along the longitudinal direction so that a total number of twenty-four nozzles is obtained once more. As can be seen in FIGS. 7a) and 7b), a further layer 36 is arranged on top of the cover layer 30 in the embodiment shown; this further layer 36 provides enlarged media reservoirs 38 on the one hand and enlarged standpipes 40 on the other other. Also these standpipes 40 fill with liquid from the media lines (not shown) due to capillary forces alone.

It should be pointed out that the media reservoirs and the media lines connected to the nozzles can be dispensed with, if the standpipes or the nozzle area can be filled with liquid directly by conventional methods, e.g. by automatic pipetting devices or microdispensers etc. If this is not possible due to an arrangement within a confined space, the larger external reservoirs will be useful, since these reservoirs can be filled very easily with standard automatic pipetting devices and since the standpipes will fill automatically through capillary forces.

The standpipes 34 and 40, respectively, which are open at the top, have the effect that the amount of liquid placed directly above the nozzle is enlarged. Other than in the case of the liquid in the media lines 26 or the liquid in the reservoirs 28, the liquid contained in the standpipes is accelerated directly towards the nozzle and is coupled thereto via a mimimum flow resistance. If the dosing head is abruptly decelerated e.g. during a downward movement, e.g. by means of the stop shown in FIG. 1, the liquid will be accelerated from the standpipes 34 and 40, respectively, directly towards the nozzle outlet, whereas the liquid contained in the reservoirs 28 must first flow through the media lines 26 in a direction transversely to the direction of acceleration. In so doing, the liquid must overcome a much higher flow resistance.

As has already been stated hereinbefore, the standpipes 34 and 40 are implemented such that they are always filled with liquid due to capillary forces. In addition to the embodiments described, in the case of which each nozzle is provided with a liquid storage area of its own, also a plurality of nozzles can form a group of nozzles and be supplied with the same liquid via a common media line. Furthermore, it is possible that a plurality of cover plates are mounted one on top of the other so as to increase the packing density of the nozzles, since the system of media lines can then be distributed to several planes. These lines in different planes can then e.g. also cross one another.

What is claimed is:

1. A device for applying at least one microdroplet to a substrate, comprising:
    a dosing head having at least one nozzle orifice and a first liquid storage area in fluid communication to the nozzle orifice; and
    a drive means for applying to the dosing head an acceleration of such a nature that, only by the fact that a quantity of liquid storage area cannot follow this acceleration due to its inertia, a microdroplet is drive out of the nozzle orifice and onto the substrate.

2. A device according to claim 1, wherein the drive means is implemented such that it is adapted to apply to the dosing head a negative acceleration adjacent the substrate while said dosing head is carrying out a movement towards said substrate.

3. A device according to claim 1, wherein the drive means is implemented such that it is adapted to apply to the dosing head an acceleration away from the substrate when said dosing head occupies a position adjacent said substrate.

4. A device according to claim 1, wherein the drive means is implemented such that it is adapted to apply to the dosing head an oscillation in such a way that the dosing head is arranged adjacent the substrate at the point of reversal of the oscillation.

5. A device according to claim 1, wherein the drive means is a piezo-bending transducer which is fixed at one end thereof and which has the dosing head attached thereto in such a way that an acceleration of said dosing head towards the substrate can be effected, a mechanical stop being additionally provided by means of which the dosing head can be decelerated abruptly adjacent the substrate.

6. A device according to claim 1, said device comprising in addition a means for producing an electrostatic field between the dosing head and the substrate.

7. A dosing head for a device according to claim 1, said dosing head comprising a dosing head body in which the at least one nozzle orifice is formed, said dosing head body including in addition a second liquid storage area which is in fluid communication with the nozzle orifice, said first liquid storage area and said nozzle orifice are formed such that, only by the fact that a quantity of liquid present in said first liquid storage area cannot follow said acceleration due to its inertia, a microdroplet can be driven out of said nozzle orifice by applying to the dosing head said acceleration.

8. A dosing head according to claim 7, wherein said second liquid storage area is formed by a standpipe extending away from the nozzle orifice in a direction opposite to the direction in which the microdroplet can be driven out of the dosing head.

9. A dosing head according to claim 7, wherein a plurality of nozzle orifices is formed in a surface of the dosing head body, each of said nozzle orifices having liquid storage areas associated therewith.

10. A dosing head according to claim 7, wherein a media reservoir for one or for a plurality of nozzle orifices is provided in the dosing head body, said media reservoir being in fluid communication with the said first liquid storage area of the respective nozzle orifice via a connection passage.

11. A dosing head according to claim 10, wherein the connection passage is implemented such that said first liquid storage area connected thereto can be filled with liquid from the media reservoir due to a capillary effect.

12. A method of applying at least one microdroplet to a substrate, said method comprising the following steps:
    a) filling a liquid storage area, which is in fluid communication with a nozzle orifice, with an amount of liquid, said nozzle orifice and said liquid storage area being formed in a dosing head; and b) applying to said dosing head an acceleration of such a nature that, only by the fact that said amount of liquid cannot follow this acceleration due to its inertia, a a microdroplet is driven out of the nozzle orifice.

13. A method according to claim 12, wherein, in step b), the dosing head is decelerated abruptly while carrying out a movement towards the substrate.

14. A method according to claim 12, wherein, in step b), the dosing head, which occupies a posit on adjacent the substrate at that time, has applied thereto an acceleration so as to cause a movement away from said substrate.

15. A method according to claim 12, wherein, in step b), the dosing head has applied thereto the acceleration by subjecting said dosing head to an oscillation.

16. A method according to claim 12, wherein step a) is carried out for a plurality of nozzle orifices which are arranged in a dosing head, the liquid storage areas associated with the nozzle orifices being filled with different analytes in such a way that an array of different analytes is produced on the substrate in step b).

* * * * *